United States Patent [19]
Orr et al.

[11] Patent Number: 5,682,894
[45] Date of Patent: Nov. 4, 1997

[54] GUIDE WIRE

[76] Inventors: Gregory C. Orr, 4926 Alameda Dr., Oceanside, Calif. 92056; Scott J. Solano, 190 Thatcher's Hill Rd., Flemington, N.J. 08822

[21] Appl. No.: 638,627

[22] Filed: Apr. 26, 1996

[51] Int. Cl.$^6$ ............................................. A61B 5/00
[52] U.S. Cl. ........................... 128/654; 128/772; 604/164
[58] Field of Search ........................... 128/654, 772; 604/164, 280, 282

[56] References Cited

U.S. PATENT DOCUMENTS

| | | | |
|---|---|---|---|
| Re. 34,695 | 8/1994 | Mar et al. | 128/772 |
| 3,789,841 | 2/1974 | Antoshkiw | 128/2.05 R |
| 4,003,369 | 1/1977 | Heilman et al. | 128/2 M |
| 4,538,622 | 9/1985 | Samson et al. | 128/772 |
| 4,554,929 | 11/1985 | Samson et al. | 128/772 |
| 4,757,827 | 7/1988 | Buchbinder et al. | 128/772 |
| 4,763,647 | 8/1988 | Gambale | 128/657 |
| 4,867,173 | 9/1989 | Leoni | 128/772 |
| 4,922,924 | 5/1990 | Gambale | 128/772 |
| 5,147,317 | 9/1992 | Shank | 604/164 |
| 5,234,003 | 8/1993 | Hall | 128/772 |
| 5,341,818 | 8/1994 | Abrams | 128/772 |
| 5,345,945 | 9/1994 | Hodgson et al. | 128/772 |
| 5,353,808 | 10/1994 | Viera | 128/772 |
| 5,409,015 | 4/1995 | Palevmo | 128/772 |
| 5,460,187 | 10/1995 | Daigle | 128/772 |

FOREIGN PATENT DOCUMENTS 0142330  4/1989  European Pat. Off. .

*Primary Examiner*—Sam Rimell
*Assistant Examiner*—Luke J. Yeh
*Attorney, Agent, or Firm*—Michael R. Shevlin; Dianne M.F. Plunkett; Harold R. Patton

[57] ABSTRACT

The present invention is for a guide wire with an improved flexible distal section with both a radiolucent coil and radiopaque coil. The guide wire comprising a core wire having a proximal end and a distal end, the proximal end of the core wire having a first diameter and the distal end having one or more reduced diameters, a radiolucent coil surrounding the reduced diameter of the core wire, the radiolucent coil having a proximal end and a distal end, the radiolucent coil having a length that is shorter than the reduced diameter of the core wire, the proximal end of the radiolucent coil being fixedly mounted to the proximal end of the reduced diameter of the core wire, a radiopaque coil surrounding the reduced diameter of the core wire, the radiopaque coil having a proximal end and a distal end, the radiopaque coil having a length that is shorter than the reduced diameter of the core wire such that the total length of the radiolucent coil and the radiopaque coil added together are approximately the same length as the reduced diameter of the core wire, the proximal end of the radiopaque coil being concentrically welded to the distal end of the radiolucent coil, the distal end of the radiopaque coil being welded to the distal end of the reduced diameter of the core wire forming a tip ball and a spring brace located distal of the welded connection between the radiolucent coil and the radiopaque coil, the spring brace attaching the radiopaque coil to the reduced diameter of the core wire.

12 Claims, 2 Drawing Sheets

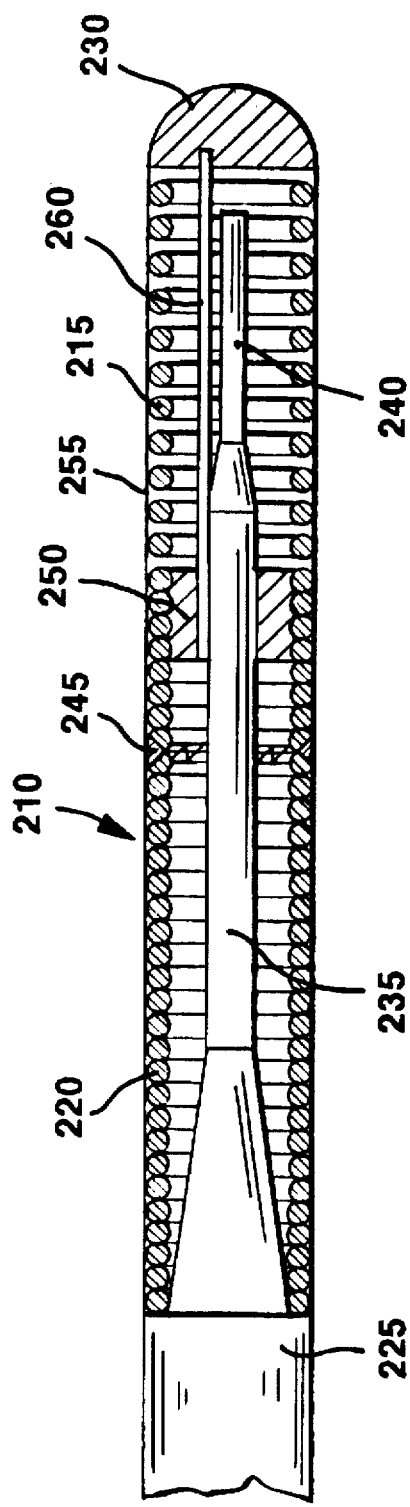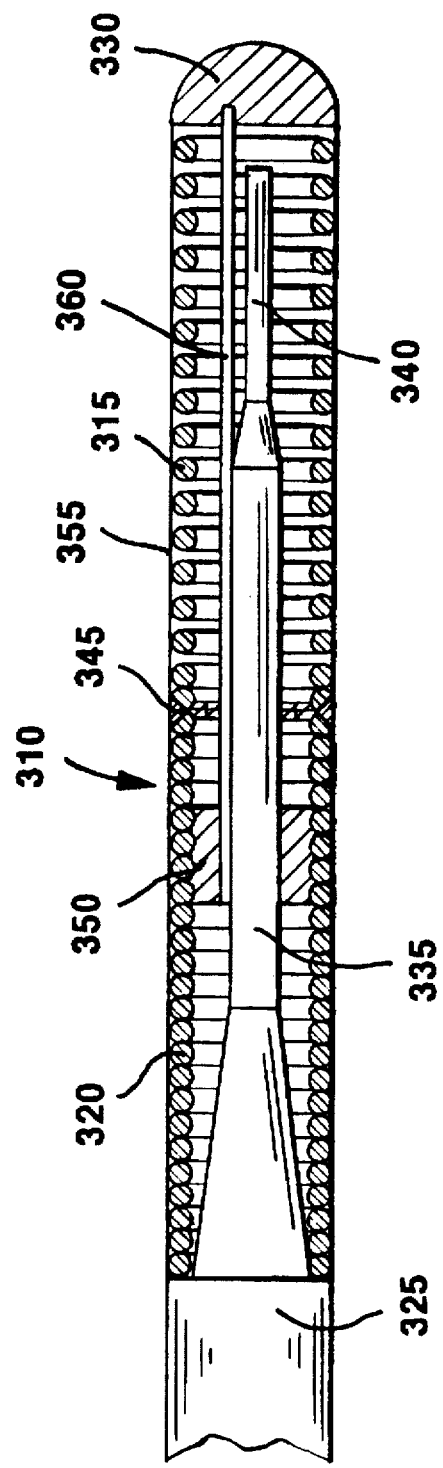

GUIDE WIRE

FIELD OF THE INVENTION

This invention relates to guide wires and more particularly to a guide wire with a flexible distal end and a radiopaque coil.

BACKGROUND OF THE INVENTION

Percutaneous transluminal coronary angioplasty (PTCA) is used to reduce arterial build-up of cholesterol fats or atherosclerotic plaque. According to this procedure, a blockage in a coronary artery can be reduced by positioning a balloon dilatation catheter across the blockage and inflating the balloon, which causes stretching of the artery and pressing of the lesion into the artery wall to re-establish acceptable blood flow through the artery. The most common catheter used is an "over-the-wire" catheter. A guide wire is first inserted into the body and advanced through the desired coronary artery to reach a stenosis. Once the guide wire is positioned beyond the stenosis, the catheter is then slid over the guide wire so that placement of the balloon spans the stenosis and the balloon is then inflated.

Generally, guide wires have a solid core wire surrounded by one or more coil springs. The tip of the guide wire is usually shapable to allow the physician to bend the guide wire tip before insertion into the artery. The ease or difficulty of using the guide wire through the artery depends on several characteristics, such as steerability and tracking. A guide wire with superior steerability and tracking is easier to direct through a tortuous path to the stenosis. During the procedure, the guide wire is tracked by using an x-ray machine. To view the guide wire using the x-ray machine, a portion of the guide wire must be formed from a radiopaque material.

There are various ways to construct a guide wire for radiopacity. One way is to use radiopaque marker bands attached to the wire. Another is to make the wire itself from radiopaque material. The most common way is to use spring coils mounted on the distal end of the guide wire that are radiopaque. There have been a number of patents directed to different constructions of guide wires including U.S. Pat. No. 4,757,827 to Buchbinder et al., U.S. Pat. No. 5,345,945 to Hodgson et al, U.S. Pat. No. 4,538,622 to Samson et al, U.S. Pat. No. Re. 34,695 to Mar et al and U.S. Pat. No. 5,353,808 to Viera.

One of the problems often encountered is that the guide wire has too long of a radiopaque section, making it very bright and blood flow difficult to see under x-ray. Some guide wires use multiple spring coils of different radiopacity. The problem with current multiple spring coil designs is at the joint between the coils. This same joint between the coils is also where the coils are joined to the core wire. This creates a non-flexible section on the wire in an area where the wire should have a smooth transition (See U.S. Pat. No. 5,345,945 and U.S. Pat. No. 5,353,808). What is needed is a guide wire that provides improved flexibility between the radiopaque and radiolucent coils and a desirable amount of radiopaqueness.

SUMMARY OF THE INVENTION

It is an object of the invention to provide a new and improved flexible distal section on a guide wire with both a radiolucent coil and radiopaque coil having the same flexibility and locating the coil to the core wire attachment point away from the coil to coil joint. The present invention is accomplished by providing a guide wire comprising a core wire having a proximal end and a distal end, the proximal end of the core wire having a first diameter and the distal end having one or more reduced diameters, a radiolucent coil surrounding the reduced diameter of the core wire, the radiolucent coil having a proximal end and a distal end, the radiolucent coil having a length that is shorter than the reduced diameter of the core wire, the proximal end of the radiolucent coil being fixedly mounted to the proximal end of the reduced diameter of the core wire, a radiopaque coil surrounding the reduced diameter of the core wire, the radiopaque coil having a proximal end and a distal end, the radiopaque coil having a length that is shorter than the reduced diameter of the core wire such that the total length of the radiolucent coil and the radiopaque coil added together are approximately the same length as the reduced diameter of the core wire, the proximal end of the radiopaque coil being concentrically welded to the distal end of the radiolucent coil, the distal end of the radiopaque coil being welded to the distal end of the reduced diameter of the core wire forming a tip ball and a welded spring brace located distal of the welded connection between the radiolucent coil and the radiopaque coil, the welded spring brace attaching the radiopaque coil to the reduced diameter of the core wire.

The advantage of a distal radiopaque coil section having the same flexibility as the proximal radiolucent coil section is that the transition between the two sections can be reduced because the coil flexibility will not change at the joint between the two sections. Varying the coil to core wire attachment point will change the overall performance of the guide wire. Moving the coil to core wire attachment point proximal of the coil to coil joint will provide more distal coil play while moving the coil to core wire attachment point distal of the coil to coil joint will provide more rigidity in the coil structure. Also disclosed is the use of the forming wire on the distal end of the guide wire. The advantage of attaching a forming wire is that shapes and dimensions can be created more easily as separate pieces than as part of a single piece of core wire. Also, the stress transmitted from the smaller, formable section to the larger, less flexible section of the core wire can be reduced with a significant bond area between the two.

BRIEF DESCRIPTION OF THE DRAWINGS

The foregoing and other features of the present invention will be best appreciated with reference to the following detailed description of a specific embodiment of the invention, when read in conjunction with the accompanying drawings.

FIG. 3 is a view showing an alternate configuration present invention assembled; and FIG. 4 is a view showing an alternate configuration present invention assembled.

DETAILED DESCRIPTION OF THE PREFERRED EMBODIMENTS

The present invention is directed to a guide wire with improved distal flexibility with both a radiolucent coil and radiopaque coil. This is accomplished by using a radiopaque coil and a radiolucent coil that have the same flexibility and locating the coil to the core wire attachment point away from the coil to coil joint. The advantage of having a distal radiopaque coil section that has the same flexibility as the proximal radiolucent coil section is that the transition between the two sections can be reduced because the coil flexibility will not change at the joint between the two sections. This will reduce the transition to that created only by the joint between the two coils and the attachment point between one coil and the core wire. A reduced transition section can assist a physician in accessing a sharp angled vascular branch by providing a smoother action as the tip of the guide wire is steered into and past the branch.

Varying the coil to core wire attachment point will change the overall performance of the guide wire. Moving the coil to core wire attachment point proximal of the coil to coil joint will provide more distal coil play. More coil play may provide a less traumatic tip and protect the core wire better. Moving the coil to core wire attachment point distal of the coil to coil joint will provide more rigidity in the coil structure, which may be desirable, for example, when crossing through a stent or calcified lesion because the coils would be less likely to snag a sharp surface. Also disclosed is the use of the forming wire on the distal end of the guide wire. The advantaged of attaching a forming wire is that shapes and dimensions can be created more easily as separate pieces than as part of a single piece of core wire. Also, the stress transmitted from the smaller, formable section to the larger, less flexible section of the core wire can be reduced with a significant bond area between the two.

Figure 1:
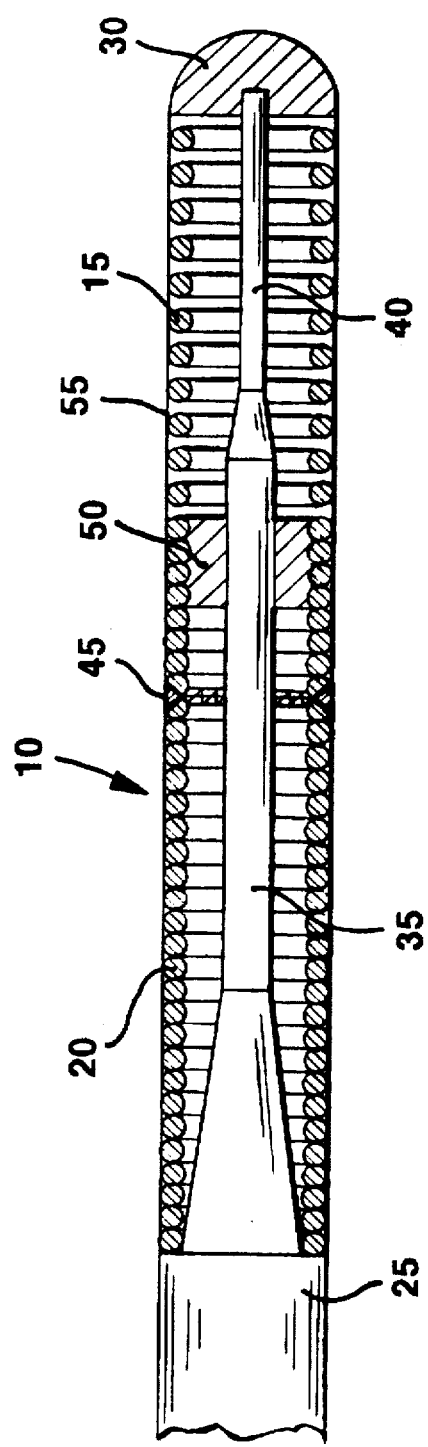
FIG. 1 is a view showing the present invention assembled.

FIG. 1 shows the distal end of the guide wire 10 consisting of a radiopaque coil 15, a radiolucent coil 20, a core wire 25 and a tip ball 30. Along the length of the guide wire 10 is a unitary torque-transmitting core wire 25 that is made from a 0.356 mm diameter (0.014") stainless steel wire, work hardened by drawing, or of shape memory wire such as nickel titanium. At the distal end of the core wire 25, the diameter is reduced with at least one step-down diameter to fit inside of the radiopaque coil 15 and the radiolucent coil 20. FIG. 1 shows a combination of multiple step-down diameters of 0.203 mm (0.008") 35 and 0.152 mm (0.006") 40. The distal end of the radiopaque coil 15, with an outer diameter of 0.356 mm (0.014") and an inner diameter of 0.254 mm (0.010") and a length 3 cm, is welded to the distal end of the step down diameter 40 of the core wire 25 forming a tip ball 30. The proximal end of the radiopaque coil 15 is then concentrically welded 45 to the distal end of the radiolucent coil 20. The radiolucent coil 20 is made of stainless steel and has an outer diameter of 0.356 mm (0.014") and an inner diameter of 0.254 mm (0.010") and a length of 26 cm. The flexibility of the radiopaque coil 15 and the radiolucent coil 20 should be approximately the same. The proximal end of the radiolucent coil 20 is attached to the proximal end of the step down diameter 35. Approximately 1 cm distal to the welded 45 connection between the radiopaque coil 15 and the radiolucent coil 20 is a welded spring brace 50 that bonds the radiopaque coil 15 to the step down diameter 35 of the core wire 25. Locating the welded spring brace 50 away from the welded 45 connection allows far greater flexibility of the distal end of the guide wire 10. The entire outside of guide wire 10 may be covered in a plastic, silicone or hydrophilic coating 55.

Figure 2:
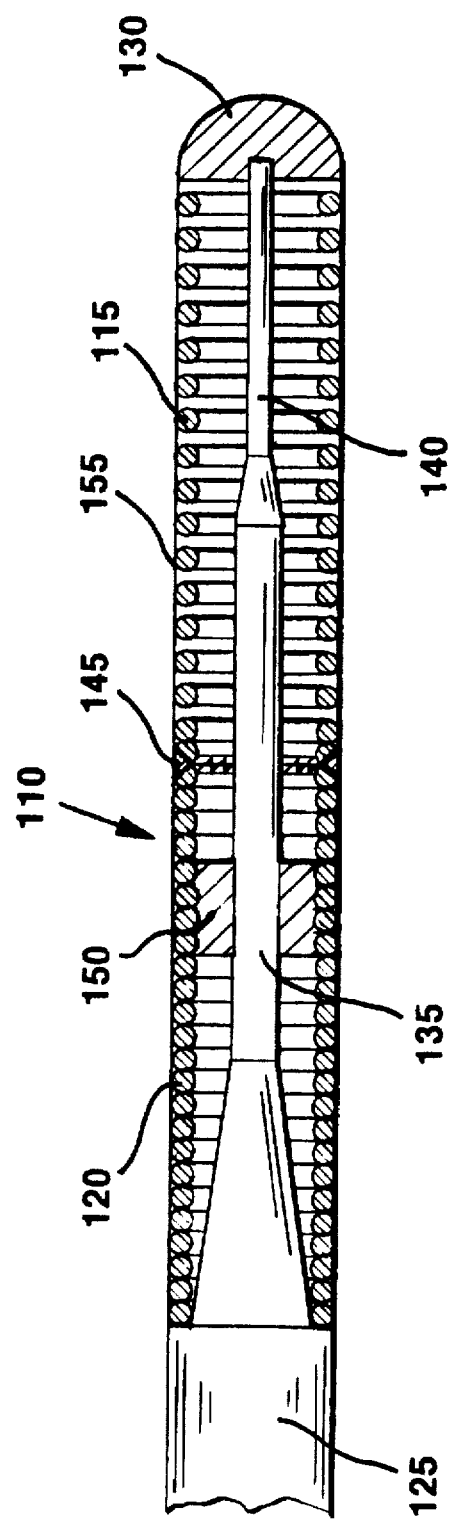
FIG. 2 is a view showing an alternate configuration present invention assembled.

FIG. 2 shows the distal end of the guide wire 110 consisting of a radiopaque coil 115, a radiolucent coil 120, a core wire 125 and a tip ball 130. This is an alternate configuration to the invention shown in FIG. 1 with the welded spring brace now located proximal to the coil connection. Along the length of the guide wire 110 is a unitary torque-transmitting core wire 125 that is made from a 0.356 mm diameter (0.014") stainless steel wire, work hardened by drawing, or of shape memory wire such as nickel titanium. At the distal end of the core wire 125, the diameter is reduced with at least one step-down diameter to fit inside of the radiopaque coil 115 and the radiolucent coil 120. FIG. 2 shows a combination of multiple step-down diameters of 0.203 mm (0.008") 135 and 0.152 mm (0.006") 140. The distal end of the radiopaque coil 115, with an outer diameter of 0.356 mm (0.014") and an inner diameter of 0.254 mm (0.010") and a length 3 cm, is welded to the distal end of the step down diameter 140 of the core wire 125 forming a tip ball 130. The proximal end of the radiopaque coil 115 is then concentrically welded 145 to the distal end of the radiolucent coil 120. The radiolucent coil 120 is made of stainless steel and has an outer diameter of 0.356 mm (0.014") and an inner diameter of 0.254 mm (0.010") and a length of 26 cm. The flexibility of the radiopaque coil 115 and the radiolucent coil 120 should be approximately the same. The proximal end of the radiolucent coil 120 is attached to the proximal end of the step down diameter 135. Approximately 1 cm proximal to the welded 145 connection between the radiopaque coil 115 and the radiolucent coil 120 is a welded spring brace 150 that bonds the radiolucent coil 120 to the step down diameter 135 of the core wire 125. Locating the welded spring brace 150 away from the welded 145 connection allows far greater flexibility of the distal end of the guide wire 110. The entire outside of guide wire 10 may be covered in a plastic, silicone or hydrophilic coating 155.

FIG. 3 shows the distal end of the guide wire 210 consisting of a radiopaque coil 215, a radiolucent coil 220, a core wire 225, a forming wire 260 and a tip ball 230. This is an alternate configuration to the invention shown in FIG. 1 except that the core wire does not extend all the way to the distal end, a forming wire does. This allows the tip for guide wire 210 to be shapeable as well as flexible. Along the length of the guide wire 210 is a torque-transmitting core wire 225 that is made from a 0.356 mm diameter (0.014") stainless steel wire, work hardened by drawing, or of shape memory wire such as nickel titanium. At the distal end of the core wire 225, the diameter is reduced with at least one step-down diameter to fit inside of the radiopaque coil 215 and the radiolucent coil 220. FIG. 3 shows a combination of multiple step-down diameters of 0.203 mm (0.008") 235 and 0.152 mm (0.006") 240. The distal end of the radiopaque coil 215, with an outer diameter of 0.356 mm (0.014") and an inner diameter of 0.254 mm (0.010") and a length 3 cm, is welded to the distal end of a forming wire 260, creating a tip ball 230. The proximal end of the radiopaque coil 215 is then concentrically welded 245 to the distal end of the radiolucent coil 220. The radiolucent coil 220 is made of stainless steel and has an outer diameter of 0.356 mm (0.014") and an inner diameter of 0.254 mm (0.010") and a length of 26 cm. The flexibility of the radiopaque coil 215 and the radiolucent coil 220 should be approximately the same. The proximal end of the radiolucent coil 220 is attached to the proximal end of the step down diameter 235. Approximately 1 cm distal to the welded 245 connection between the radiopaque coil 215 and the radiolucent coil 220 is a welded spring brace 250 that bonds the radiopaque coil 215 to the step down diameter 235 of the core wire 225 and the forming wire 260 such that the proximal end of the forming wire 260 is joined to the welded spring brace 250 and the distal end of the forming wire 260 is joined the to tip ball 230. The forming wire 260 may be round, square or rectangular in shape. The entire outside of the guide wire 210 may be covered with a plastic, silicone or hydrophilic coating 255.

FIG. 4 shows the distal end of the guide wire 310 consisting of a radiopaque coil 315, a radiolucent coil 320, a core wire 325, a formable wire 360 and a tip ball 330. This is an alternate configuration to the invention shown in FIG. 3 with the welded spring brace now located proximal to the coil connection. Along the length of the guide wire 310 is a torque-transmitting core wire 325 that is made from a 0.356 mm diameter (0.014") stainless steel wire, work hardened by drawing, or of shape memory wire such as nickel titanium. At the distal end of the core wire 325, the diameter is reduced with at least one step-down diameter to fit inside of the radiopaque coil 315 and the radiolucent coil 320. FIG. 4 shows a combination of multiple step-down diameters of 0.203 mm (0.008") 335 and 0.152 mm (0.006") 340. The distal end of the radiopaque coil 315, with an outer diameter of 0.356 mm (0.014") and an inner diameter of 0.254 mm (0.010") and a length 3 cm, is welded to the distal end of a forming wire 360, creating a tip ball 330. The proximal end of the radiopaque coil 315 is then concentrically welded 345 to the distal end of the radiolucent coil 320. The radiolucent coil 320 is made of stainless steel and has an outer diameter of 0.356 mm (0.014") and an inner diameter of 0.254 mm (0.010") and a length of 26 cm. The flexibility of the radiopaque coil 315 and the radiolucent coil 320 should be approximately the same. The proximal end of the radiolucent coil 320 is attached to the proximal end of the step down diameter 335. Approximately 1 cm proximal to the welded 345 connection between the radiopaque coil 315 and the radiolucent coil 320 is a welded spring brace 350 that bonds the radiolucent coil 320 to the step down diameter 335 of the core wire 325 and the forming wire 360 such that the proximal end of the forming wire 360 is joined to the welded spring brace 350 and the distal end of the forming wire 360 is joined the to tip ball 330. The forming wire 360 may be round, square or rectangular in shape. The entire outside of the guide wire 310 may be covered with a plastic, silicone or hydrophilic coating 355.

The preceding specific embodiments are illustrative of the practice of the invention. It is to be understood, however, that other expedients known to those skilled in the art or disclosed herein, may be employed without departing from the scope of the appended claims.

| No. | Component |
| --- | --- |
| 10 | Guide Wire |
| 15 | Radiopaque coil |
| 20 | Radiolucent coil |
| 25 | Core Wire |
| 30 | Tip Ball |
| 35 | Step-down Diameter — Core Wire |
| 40 | Step-down Diameter — Core Wire |
| 45 | Weld — Radiopaque Coil to Radiolucent Coil |
| 50 | Welded Spring Brace |
| 55 | Plastic, Silicone or Hydrophilic Coating |
| 110 | Guide Wire |
| 115 | Radiopaque coil |
| 120 | Radiolucent coil |
| 125 | Core Wire |
| 130 | Tip Ball |
| 135 | Step-down Diameter — Core Wire |
| 140 | Step-down Diameter — Core Wire |
| 145 | Weld — Radiopaque Coil to Radiolucent Coil |
| 150 | Welded Spring Brace |
| 155 | Plastic, Silicone or Hydrophilic Coating |
| 210 | Guide Wire |
| 215 | Radiopaque coil |
| 220 | Radiolucent coil |
| 225 | Core Wire |
| 230 | Tip Ball |
| 235 | Step-down Diameter — Core Wire |
| 240 | Step-down Diameter — Core Wire |
| 245 | Weld — Radiopaque Coil to Radiolucent Coil |
| 250 | Welded Spring Brace |
| 255 | Plastic, Silicone or Hydrophilic Coating |
| 260 | Forming Wire |
| 310 | Guide Wire |
| 315 | Radiopaque coil |
| 320 | Radiolucent coil |
| 325 | Core Wire |
| 330 | Tip Ball |
| 335 | Step-down Diameter — Core Wire |
| 340 | Step-down Diameter — Core Wire |
| 345 | Weld — Radiopaque Coil to Radiolucent Coil |
| 350 | Welded Spring Brace |
| 355 | Plastic, Silicone or Hydrophilic Coating |
| 360 | Forming Wire |

What is claimed is:

1. A guide wire comprising:
   (a) a core wire having a proximal end and a distal end, the proximal end of the core wire having a first diameter and the distal end having one or more reduced diameters;
   (b) a radiolucent coil surrounding the reduced diameter of the core wire, the radiolucent coil having a proximal end and a distal end, the radiolucent coil having a length that is shorter than the length of the reduced diameter of the core wire, the proximal end of the radiolucent coil being fixedly mounted to the proximal end of the reduced diameter of the core wire;
   (c) a radiopaque coil surrounding the reduced diameter of the core wire, the radiopaque coil having a proximal end and a distal end, the radiopaque coil having a length that is shorter than the length of the reduced diameter of the core wire such that the total length of the radiolucent coil and the radiopaque coil added together are approximately the same length as the reduced diameter of the core wire, the proximal end of the radiopaque coil being concentrically welded to the distal end of the radiolucent coil, the distal end of the radiopaque coil being welded to the distal end of the reduced diameter of the core wire forming a tip ball; and
   (d) a welded spring brace located distal of the welded connection between the radiolucent coil and the radiopaque coil, the welded spring brace attaching the radiopaque coil to the reduced diameter of the core wire.

2. The guide wire of claim 1 wherein the radiolucent coil and the radiopaque coil have the same flexibility.

3. A guide wire comprising:
   (a) a core wire having a proximal end and a distal end, the proximal end of the core wire having a first diameter and the distal end having one or more reduced diameters;
   (b) a radiolucent coil surrounding the reduced diameter of the core wire, the radiolucent coil having a proximal end and a distal end, the radiolucent coil having a length that is shorter than the length of the reduced diameter of the core wire, the proximal end of the radiolucent coil being fixedly mounted to the proximal end of the reduced diameter of the core wire;
   (c) a radiopaque coil surrounding the reduced diameter of the core wire, the radiopaque coil having a proximal end and a distal end, the radiopaque coil having a length that is shorter than the length of the reduced diameter of the core wire such that the total length of the radiolucent coil and the radiopaque coil added together are approximately the same length as the reduced diameter of the core wire, the proximal end of the radiopaque coil being concentrically welded to the distal end of the radiolucent coil, the distal end of the radiopaque coil being welded to the distal end of the reduced diameter of the core wire forming a tip ball; and (d) a welded spring brace located proximal of the welded connection between the radiolucent coil and the radiopaque coil, the welded spring brace attaching the radiolucent coil to the reduced diameter of the core wire.

4. The guide wire of claim 3 wherein the radiolucent coil and the radiopaque coil have the same flexibility.

5. A guide wire comprising:

(a) a core wire having a proximal end and a distal end, the proximal end of the core wire having a first diameter and the distal end having one or more reduced diameters;

(b) a radiolucent coil surrounding the reduced diameter of the core wire, the radiolucent coil having a proximal end and a distal end, the radiolucent coil having a length that is shorter than the length of the reduced diameter of the core wire, the proximal end of the radiolucent coil being fixedly mounted to the proximal end of the reduced diameter of the core wire;

(c) a radiopaque coil surrounding the reduced diameter of the core wire, the radiopaque coil having a proximal end and a distal end, the radiopaque coil having a length that is shorter than the length of the reduced diameter of the core wire such that the total length of the radiolucent coil and the radiopaque coil added together is longer than the length of the reduced diameter of the core wire, the proximal end of the radiopaque coil being concentrically welded to the distal end of the radiolucent coil;

(d) a forming wire having a proximal end and a distal end, the distal end of the forming wire being welded to the distal end of the radiopaque coil forming a tip ball; and (e) a welded spring brace located distal of the welded connection between the radiolucent coil and the radiopaque coil, the welded spring brace attaching the radiopaque coil with the reduced diameter of the core wire and the proximal end of the forming wire.

6. The guide wire of claim 5 wherein the radiolucent coil and the radiopaque coil have the same flexibility.

7. A guide wire comprising:

(a) a core wire having a proximal end and a distal end, the proximal end of the core wire having a first diameter and the distal end having one or more reduced diameters;

(b) a radiolucent coil surrounding the reduced diameter of the core wire, the radiolucent coil having a proximal end and a distal end, the radiolucent coil having a length that is shorter than the length of the reduced diameter of the core wire, the proximal end of the radiolucent coil being fixedly mounted to the proximal end of the reduced diameter of the core wire;

(c) a radiopaque coil surrounding the reduced diameter of the core wire, the radiopaque coil having a proximal end and a distal end, the radiopaque coil having a length that is shorter than the length of the reduced diameter of the core wire such that the total length of the radiolucent coil and the radiopaque coil added together is longer than the length of the reduced diameter of the core wire, the proximal end of the radiopaque coil being concentrically welded to the distal end of the radiolucent coil;

(d) a forming wire having a proximal end and a distal end, the distal end of the forming wire being welded to the distal end of the radiopaque coil forming a tip ball; and (e) a welded spring brace located proximal of the welded connection between the radiolucent coil and the radiopaque coil, the welded spring brace attaching the radiolucent coil with the reduced diameter of the core wire and the proximal end of the forming wire.

8. The guide wire of claim 7 wherein the radiolucent coil and the radiopaque coil have the same flexibility.

9. A guide wire comprising:

(a) a core wire having a proximal end and a distal end, the proximal end of the core wire having a first diameter and the distal end having one or more reduced diameters;

(b) a radiolucent coil surrounding the reduced diameter of the core wire, the radiolucent coil having a proximal end and a distal end, the radiolucent coil having a length that is shorter than the length of the reduced diameter of the core wire, the proximal end of the radiolucent coil being fixedly mounted to the proximal end of the reduced diameter of the core wire;

(c) a radiopaque coil surrounding the reduced diameter of the core wire, the radiopaque coil having a proximal end and a distal end, the radiopaque coil and the radiolucent coil having the same flexibility, the radiopaque coil having a length that is shorter than the length of the reduced diameter of the core wire such that the total length of the radiolucent coil and the radiopaque coil added together are approximately the same length as the reduced diameter of the core wire, the proximal end of the radiopaque coil being concentrically welded to the distal end of the radiolucent coil, the distal end of the radiopaque coil being welded to the distal end of the reduced diameter of the core wire forming a tip ball; and (d) a welded spring brace located distal of the welded connection between the radiolucent coil and the radiopaque coil, the welded spring brace attaching the radiopaque coil to the reduced diameter of the core wire.

10. A guide wire comprising:

(a) a core wire having a proximal end and a distal end, the proximal end of the core wire having a first diameter and the distal end having one or more reduced diameters;

(b) a radiolucent coil surrounding the reduced diameter of the core wire, the radiolucent coil having a proximal end and a distal end, the radiolucent coil having a length that is shorter than the length of the reduced diameter of the core wire, the proximal end of the radiolucent coil being fixedly mounted to the proximal end of the reduced diameter of the core wire;

(c) a radiopaque coil surrounding the reduced diameter of the core wire, the radiopaque coil having a proximal end and a distal end, the radiopaque coil and the radiolucent coil having the same flexibility, the radiopaque coil having a length that is shorter than the length of the reduced diameter of the core wire such that the total length of the radiolucent coil and the radiopaque coil added together are approximately the same length as the reduced diameter of the core wire, the proximal end of the radiopaque coil being concentrically welded to the distal end of the radiolucent coil, the distal end of the radiopaque coil being welded to the distal end of the reduced diameter of the core wire forming a tip ball; and (d) a welded spring brace located proximal of the welded connection between the radiolucent coil and the radiopaque coil, the welded spring brace attaching the radiolucent coil to the reduced diameter of the core wire.

11. A guide wire comprising:

(a) a core wire having a proximal end and a distal end, the proximal end of the core wire having a first diameter and the distal end having one or more reduced diameters;

(b) a radiolucent coil surrounding the reduced diameter of the core wire, the radiolucent coil having a proximal end and a distal end, the radiolucent coil having a length that is shorter than the length of the reduced diameter of the core wire, the proximal end of the radiolucent coil being fixedly mounted to the proximal end of the reduced diameter of the core wire;

(c) a radiopaque coil surrounding the reduced diameter of the core wire, the radiopaque coil having a proximal end and a distal end, the radiopaque coil and the radiolucent coil having the same flexibility, the radiopaque coil having a length that is shorter than the length of the reduced diameter of the core wire such that the total length of the radiolucent coil and the radiopaque coil added together is longer than the length of the reduced diameter of the core wire, the proximal end of the radiopaque coil being concentrically welded to the distal end of the radiolucent coil;

(d) a forming wire having a proximal end and a distal end, the distal end of the forming wire being welded to the distal end of the radiopaque coil forming a tip ball; and (e) a welded spring brace located distal of the welded connection between the radiolucent coil and the radiopaque coil, the welded spring brace attaching the radiopaque coil with the reduced diameter of the core wire and the proximal end of the forming wire.

12. A guide wire comprising:

(a) a core wire having a proximal end and a distal end, the proximal end of the core wire having a first diameter and the distal end having one or more reduced diameters;

(b) a radiolucent coil surrounding the reduced diameter of the core wire, the radiolucent coil having a proximal end and a distal end, the radiolucent coil having a length that is shorter than the length of the reduced diameter of the core wire, the proximal end of the radiolucent coil being fixedly mounted to the proximal end of the reduced diameter of the core wire;

(c) a radiopaque coil surrounding the reduced diameter of the core wire, the radiopaque coil having a proximal end and a distal end, the radiopaque coil and the radiolucent coil having the same flexibility, the radiopaque coil having a length that is shorter than the length of the reduced diameter of the core wire such that the total length of the radiolucent coil and the radiopaque coil added together is longer than the length of the reduced diameter of the core wire, the proximal end of the radiopaque coil being concentrically welded to the distal end of the radiolucent coil;

(d) a forming wire having a proximal end and a distal end, the distal end of the forming wire being welded to the distal end of the radiopaque coil forming a tip ball; and (e) a welded spring brace located proximal of the welded connection between the radiolucent coil and the radiopaque coil, the welded spring brace attaching the radiolucent coil with the reduced diameter of the core wire and the proximal end of the forming wire.

\* \* \* \* \*